(12) United States Patent
Kariya et al.

(10) Patent No.: US 8,980,588 B2
(45) Date of Patent: Mar. 17, 2015

(54) METHOD FOR PRODUCING ACRYLAMIDE USING MICROBIAL CATALYST

(75) Inventors: Takamitsu Kariya, Yokohama (JP); Hiroyasu Banba, Yokohama (JP); Makoto Kano, Yokohama (JP)

(73) Assignee: Mitsubishi Rayon Co., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 13/518,125

(22) PCT Filed: Dec. 21, 2010

(86) PCT No.: PCT/JP2010/073038
§ 371 (c)(1),
(2), (4) Date: Jun. 21, 2012

(87) PCT Pub. No.: WO2011/078184
PCT Pub. Date: Jun. 30, 2011

(65) Prior Publication Data
US 2012/0276601 A1 Nov. 1, 2012

(30) Foreign Application Priority Data
Dec. 25, 2009 (JP) .................. 2009-294613

(51) Int. Cl.
*C12P 13/02* (2006.01)
*C12M 1/00* (2006.01)
(52) U.S. Cl.
CPC ............... *C12P 13/02* (2013.01); *C12M 29/06* (2013.01)
USPC ........................................................ 435/129
(58) Field of Classification Search
None
See application file for complete search history.

(56) References Cited

U.S. PATENT DOCUMENTS

| | | | |
|---|---|---|---|
| 4,248,968 | A | 2/1981 | Watanabe et al. |
| 7,309,590 | B2 | 12/2007 | Petersen et al. |
| 2004/0048348 | A1 | 3/2004 | Murao et al. |
| 2004/0219647 | A1 | 11/2004 | Murao et al. |
| 2008/0108770 | A1* | 5/2008 | Ishii et al. .................. 526/303.1 |

FOREIGN PATENT DOCUMENTS

| | | |
|---|---|---|
| JP | 56-045755 | 4/1981 |
| JP | 59-232096 | 12/1984 |
| JP | 63-146778 | 6/1988 |
| JP | 06-062831 | 3/1994 |
| JP | 07-265091 | 10/1995 |
| JP | 3030699 | 8/1996 |
| JP | 11-089575 | 4/1999 |
| JP | 11-123098 | 5/1999 |
| JP | 2000-106864 | 4/2000 |
| JP | 2001-340091 | 12/2001 |
| JP | 2004-524047 | 8/2004 |
| WO | WO 02/50297 | 6/2002 |
| WO | WO 02/088373 | 11/2002 |
| WO | WO 03/000914 | 1/2003 |
| WO | WO 2009/113654 | 9/2009 |

OTHER PUBLICATIONS

Mavros et al., "Investigation bylaser Doppler velocimetryof the e$ects of liquid flow rates and feed positions on the (ow patterns induced in a stirred tank byan axial-flow impeller", Chemical Engineering Science 57 (2002) 3939-3952.*
Samaras et al., "Effect of Continuous Feed Stream and Agitator Type on CFSTR Mixing State", Ind. Eng. Chem. Res. 2006, 45, 4805-4815.*
Merriam-Webster definition of "volatile"—retrieved from < http://www.merriam-webster.com/dictionary/volatile > on Aug. 15, 2014.*
Ineos Nitriles, Acrylontirile, 2006, retrieved from < http://www.ineos.com/Global/Nitriles/Products/Technical%20Information/ER-AN-ReB.pdf > on Aug. 15, 2014.*
International Search Report dated Apr. 5, 2011 issued to priority international application No. PCT/JP2010/073038.

* cited by examiner

*Primary Examiner* — Suzanne M Noakes
(74) *Attorney, Agent, or Firm* — Knobbe, Martens, Olson & Bear LLP

(57) ABSTRACT

A method for producing acrylamide from acrylonitrile by a biocatalyst method, wherein both evaporation of acrylonitrile into a gas phase and damaging of a catalyst by stirring are prevented, is provided. In the present invention, the production of acrylamide from acrylonitrile by the biocatalyst method comprises feeding acrylonitrile into an aqueous medium comprising a microbial catalyst.

1 Claim, 2 Drawing Sheets

METHOD FOR PRODUCING ACRYLAMIDE USING MICROBIAL CATALYST

CROSS-REFERENCE TO RELATED APPLICATIONS

This application is the U.S. National Phase under 35 U.S.C. §371 of International Application PCT /JP2010/073038, filed Dec. 21, 2010, which was published in a non-English language, which claims priority to JP 2009-294613, filed Dec. 25, 2009.

TECHNICAL FIELD

The present invention relates to a method for producing acrylamide from acrylonitrile by an action of nitrile hydratase derived from a microorganism.

BACKGROUND ART

Acrylamide is used as an industrially important substance in a wide range of areas. For example, acrylamide polymers are widely used as flocculants for wastewater treatment, paper strength agents, oil recovery agents and the like. Acrylamide has been conventionally industrially produced by hydrating the corresponding acrylonitrile using reduced copper as a catalyst. Recently, however, a method using a microbial catalyst instead of a copper catalyst (biocatalyst method) has been developed and partially practically used.

Since the biocatalyst method requires only mild reaction conditions, hardly produces by-products, and allows construction of a very simple process, it has been regarded as a hopeful industrial production method, and many microorganisms having an enzyme that has the catalytic ability to convert acrylonitrile into acrylamide by hydration (enzyme name: nitrile hydratase) have been discovered so far. Various methods are known as methods of production of acrylamide using a microbial catalyst (see Patent Documents 1 to 8, for example).

On the other hand, since acrylonitrile has lower solubility in water or an aqueous acrylamide solution (7.3 g/100 g of water, 25° C.), in cases where dissolution of acrylonitrile in water is insufficient, adverse effects are caused, such as decreased catalyst productivity or deterioration of a microbial catalyst due to insufficient contact between acrylonitrile and the microbial catalyst, and increased loss of acrylonitrile by evaporation into the gas phase. The solubility of acrylonitrile in water or an aqueous acrylamide solution can be enhanced by vigorously stirring the aqueous medium or the reaction liquid. However, such vigorous stirring may damage the microbial catalyst, resulting in decreased activity.

In order to solve these problems, for example, Patent Document 1 describes that it is appropriate to add acrylonitrile or methacrylonitrile dropwise to the reaction system with stirring such that the substrate is always in the dissolved state in the reaction system. Further, Patent Document 2 discloses a method for producing an amide compound from a nitrile compound using a biocatalyst whose production cost and environmental load are suppressed, wherein contact and dispersibility of a nitrile compound and a biocatalyst are improved by setting the stirring power requirement to 0.08 to 1.3 kW/m$^3$. Further, Patent Document 3 discloses an apparatus for producing an aqueous acrylamide solution, which apparatus comprises a reactor having a circulation route equipped with a pump, in which a part of the reaction mixture is circulated by the pump and at least one heat exchanger is provided. As a best mode, addition of acrylonitrile to the circulation route equipped with a pump is disclosed in the document. Further, Patent Document 4 describes that it is important to use an appropriate mixing device such as a rotor or line mixer to sufficiently mix the aqueous medium phase and the nitrile phase, which are separated into two layers when these are left to stand.

However, as can be seen in the above Patent Documents, prevention of both evaporation of acrylonitrile into the gas phase and damaging of the catalyst were still insufficient in the conventional techniques. Further, the method in Patent Document 3 requires much energy for producing power, and also requires additional cost for removal of heat due to possible generation of circulating heat by the pump. Further, the microbial catalyst is likely to be damaged by a vortex flow generated by the pump, resulting in decreased activity, which is problematic. Thus, effective means in the biocatalyst method that allow prevention of both evaporation of acrylonitrile into the gas phase and damaging of the catalyst still need to be studied.

PRIOR ART DOCUMENTS

Patent Documents

Patent Document 1: JP 56-38118 B
Patent Document 2: WO 09/113654
Patent Document 3: Japanese Translated PCT Patent Application Laid-open No. 2004-524047
Patent Document 4: JP 11-89575 A
Patent Document 5: JP 11-123098 A
Patent Document 6: JP 7-265091 A
Patent Document 7: WO 03/000914
Patent Document 8: JP 2001-340091 A

SUMMARY OF THE INVENTION

Problems to be Solved by the Invention

The present invention provides a method for producing acrylamide from acrylonitrile by the biocatalyst method, wherein both evaporation of acrylonitrile into the gas phase and damaging of the catalyst by stirring are prevented.

Means for Solving the Problems

The present inventors discovered that, in contrast to the fact that acrylonitrile is especially prone to polymerize when it is in the liquid state, polymerization is less likely to occur in cases where acrylonitrile is fed to an aqueous medium under reaction conditions for the biocatalyst method, and gentle stirring is sufficient for quick dispersion and dissolution of acrylonitrile in the aqueous medium, thereby completing the present invention.

That is, the present invention provides a method for producing acrylamide in an aqueous medium by feeding acrylonitrile to the aqueous medium supplemented with a microbial catalyst while stirring the aqueous medium, the method comprising: placing, in the aqueous medium, a feed opening of an acrylonitrile feed tube that feeds acrylonitrile to the aqueous medium; and feeding acrylonitrile into the aqueous medium.

Further, the present invention provides the above method for producing acrylamide, wherein the feed opening has an opening area smaller than the cross-sectional area of the acrylonitrile feed tube.

Effect of the Invention

According to the present invention, acrylonitrile can be added such that it is always in the dissolved state in the reaction system; acrylonitrile hardly evaporates to the outside of the reaction system; and damaging of the microbial catalyst by stirring can be prevented. Therefore, by the present invention, high contacting efficiency with the microbial catalyst can be achieved, and acrylamide can be produced at low cost, with less energy, with less environmental load and at high productivity.

Further, in the present invention, the above-described feed opening preferably has a smaller opening area than the cross-sectional area of the acrylonitrile feed tube, in order to obtain a higher effect in view of enhancement of the yield of acrylamide.

DESCRIPTION OF THE EMBODIMENTS

Figure 1:
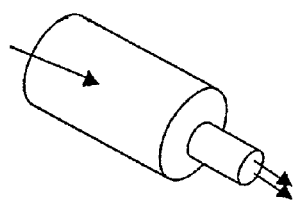
FIG. 1 is a diagram showing an embodiment of the feed opening of the acrylonitrile feed tube of the present invention.

In the method of the present invention for producing acrylamide, acrylonitrile is fed to an aqueous medium supplemented with a microbial catalyst while the aqueous medium is stirred, to produce acrylamide in the aqueous medium, which method comprises: placing, in the aqueous medium, a feed opening of an acrylonitrile feed tube that feeds acrylonitrile to the aqueous medium; and feeding acrylonitrile into the aqueous medium.

In the method of the present invention for producing acrylamide, acrylonitrile is brought into contact with a microbial catalyst(s) in an aqueous medium to produce acrylamide. The method of the present invention for producing acrylamide may be carried out in the same manner as a known technique for production of acrylamide by the biocatalyst method except that a feed opening of an acrylonitrile feed tube is placed in an aqueous medium to feed acrylonitrile into the aqueous medium, as long as the effect of the present invention can be obtained.

The aqueous medium is a liquid comprising water as a major component. The aqueous medium may comprise, in addition to a microbial catalyst, other components such as a pH-buffering agent.

The microbial catalyst means a microorganism that expresses and retains nitrile hydratase, which is an enzyme having the action to convert a nitrile compound to an amide compound; or a product prepared by processing the enzyme or the microorganism. Examples of the microorganism include those belonging to *Nocardia, Corynebacterium, Bacillus, Pseudomonas, Micrococcus, Rhodococcus, Acinetobacter, Xanthobacter, Streptomyces, Rhizobium, Klebsiella, Enterobacter, Erwinia, Aeromonas, Citrobacter, Achromobacter, Agrobacterium* and *Pseudonocardia.*

Examples of the processed product include chemically processed products of the cell of the microorganism or the enzyme, and the cell of the microorganism or the enzyme that is immobilized on a carrier. Examples of such processed products include the microorganism cell or the enzyme encapsulated in a fine mesh of a polymer gel, the microorganism cell or the enzyme coated with a semi-permeable polymer coat, the enzyme cross-linked with a reagent having 2 or more functional groups, and the enzyme bound to a water-insoluble carrier.

Examples of the carrier include glass beads, silica gel, polyurethane, polyacrylamide, polyvinyl alcohol, carrageenan, alginic acid, agar and gelatin.

The concentration of the microbial catalyst in the aqueous medium is not restricted as long as a desired degree of conversion from acrylonitrile to acrylamide or a desired yield of acrylamide can be achieved, and may be appropriately selected such that 5 to 500 mg of dry cells are contained in 1 L of the aqueous medium.

The above-described stirring at least allows dispersion of acrylonitrile that was fed to the aqueous medium, without formation of a layer on the surface of the aqueous medium. The stirring is preferably carried out at a tip speed of not more than 4.0 m/s in view of prevention of damaging of the microbial catalyst. As the stirring blade for the stirring, various stirring blades may be used. Examples of the stirring blade include paddles, disk turbines, propellers, helical ribbons, anchors, Pfaudler and fan turbines.

The stirring is preferably carried out at a Froude number of 0.05 to 0.20, more preferably carried out at a Froude number of 0.08 to 0.16 in view of good dispersion of acrylonitrile in the aqueous medium and suppression of evaporation of acrylonitrile into the gas phase. The Froude number (Fr) herein means the ratio between the inertial force and the gravity of the aqueous medium to be stirred and is a dimensionless number that influences the extent of disturbance of the interface between the liquid surface and the gas phase, which number is represented by the following equation.

$$Fr = n^2 d/g$$

In this equation, n represents the rotation rate [1/s]; d represents the stirring blade diameter [m]; and g represents the gravitational acceleration [m/s$^2$].

Further, the above-described stirring is preferably carried out with a stirring power requirement of 0.02 to 1.0 kW/m$^3$ per unit volume of the aqueous medium in view of reduction in the energy consumption.

The reaction temperature for the production of acrylamide in the present invention is preferably 5 to 40° C., more preferably 20 to 35° C. in view of obtaining sufficient reaction activity of the microbial catalyst and suppressing deactivation of the microbial catalyst.

In the present invention, acrylonitrile may be fed to the aqueous medium such that a layer is not formed by acrylonitrile remaining unconsumed by the reaction after being fed. Acrylonitrile may be fed to the aqueous medium either continuously or intermittently. The feeding of acrylonitrile can be controlled based on the concentration of acrylonitrile in the aqueous medium, and acrylonitrile is preferably fed such that the concentration of acrylonitrile in the aqueous medium is 0.1 to 5.0%, more preferably fed such that the concentration of acrylonitrile in the aqueous medium is 1.0 to 2.5%.

The position of the feed opening of the acrylonitrile feed tube may be in the aqueous medium. If the position of the liquid surface of the aqueous medium is defined as 0% and the depth of the deepest part of the aqueous medium is defined as 100%, the position of the feed opening is preferably not more than 80%, more preferably not more than 60%, still more preferably not more than 50%, in view of enhancement of the yield of acrylamide. The acrylonitrile feed tube may have either one or more feed openings.

Further, by placing the feed opening near the stirring blade for stirring the aqueous medium, the rate of dissolution of acrylonitrile can be further enhanced. In view of this, in cases of industrial production of acrylamide according to the present invention, the feed opening is positioned at preferably not more than 50 cm distant, more preferably not more than 30 cm distant, still more preferably not more than 20 cm distant from the tip of the stirring blade. Further, in cases where a plurality of stirring blades are used, it is also preferred to place the feed opening between the stirring blades.

In industrial production of acrylamide according to the present invention, in view of promotion of dispersion and dissolution of acrylonitrile in the aqueous medium, acrylonitrile is preferably fed from the acrylonitrile feed tube to the aqueous medium such that the linear velocity of acrylonitrile at the feed opening is not less than 0.05 m/s, more preferably fed from the acrylonitrile feed tube to the aqueous medium such that the linear velocity of acrylonitrile at the feed opening is not less than 0.1 m/s. From this viewpoint, the cross-sectional area of the feed opening is preferably as small as possible within the range in which the desired feed rate of acrylonitrile can be achieved.

In industrial production of acrylamide according to the present invention, in view of reducing pressure loss during feeding of acrylonitrile, acrylonitrile is preferably fed from the acrylonitrile feed tube to the aqueous medium such that the linear velocity of acrylonitrile in the acrylonitrile feed tube is not more than 3 m/s, more preferably fed from the acrylonitrile feed tube to the aqueous medium such that the linear velocity of acrylonitrile in the acrylonitrile feed tube is not more than 1.5 m/s. From this viewpoint, the cross-sectional area of the acrylonitrile feed tube is preferably as large as possible.

Figure 2:
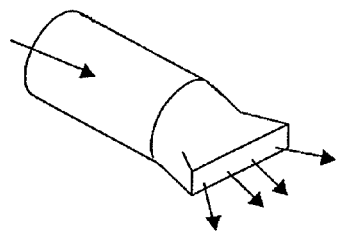
FIG. 2 is a diagram showing another embodiment of the feed opening of the acrylonitrile feed tube of the present invention.

The above-described linear velocity of acrylonitrile in the acrylonitrile feed tube can be realized by using, for the acrylonitrile feed tube, a tube having an appropriate tube diameter depending on the feed rate of acrylonitrile. The above-described linear velocity of acrylonitrile at the feed opening can be realized by setting the cross-sectional area of the feed opening smaller compared to the cross-sectional area of the acrylonitrile feed tube. For example, the cross-sectional area of the feed opening can be reduced by connecting, as shown in FIG. 1, a tube having a cross-sectional area smaller than that of the acrylonitrile feed tube to the tip of the acrylonitrile feed tube; by flatten, as shown in FIG. 2, the tip of the acrylonitrile feed tube; or by sealing the tip of the acrylonitrile feed tube and opening at the tip a hole with a diameter smaller than the inner diameter of the feed tube.

The acrylonitrile feed tube and the feed opening may be formed with a material(s) that do/does not substantially affect acrylonitrile and/or production of acrylamide. Examples of such a material(s) include stainless steel, copper, polyethylene, polypropylene and fluorocarbon resins.

The production method of the present invention may be carried out either by a method based on continuous reaction (method wherein acrylamide is continuously produced) or by a method based on batch reaction (method wherein acrylamide is discontinuously produced).

The method by continuous reaction herein means a method to continuously produce acrylamide by continuously or intermittently feeding acrylonitrile as a raw material and a microbial catalyst to a reaction vessel and continuously or intermittently removing an aqueous medium containing the reaction product, without entirely removing the reaction mixture in the reaction vessel.

Figure 3:
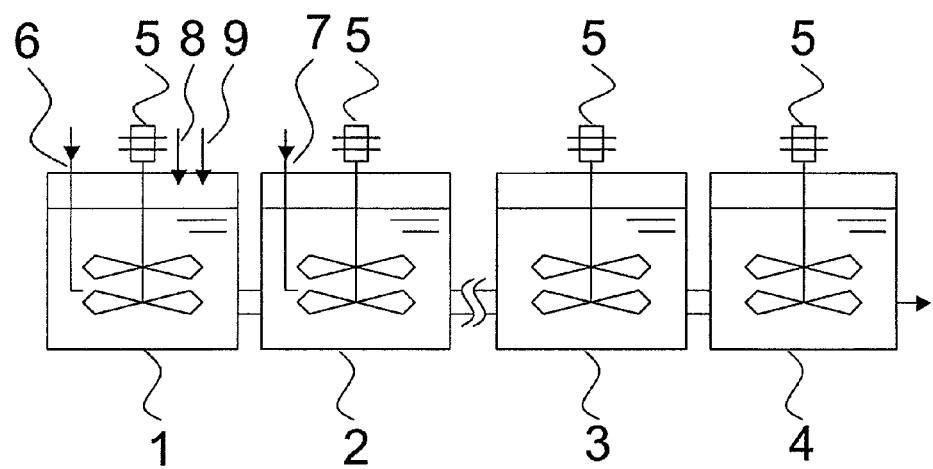
FIG. 3 is a diagram showing an example of the reaction apparatus used in the present invention.

The method by continuous reaction may be carried out by, for example, using an apparatus having a plurality of reaction vessels that are connected in series as shown in FIG. 3. The number of the reaction vessels is preferably as large as possible in view of precisely controlling the reaction depending on the concentrations of acrylonitrile and acrylamide in the aqueous medium, while the number is preferably as small as possible in view of suppressing the cost of the apparatus and in view of preventing complication of the reaction control. Based on these viewpoints, the number of the reaction vessels is preferably 2 to 20, more preferably 3 to 15, still more preferably 3 to 10.

The apparatus shown in FIG. 3 has a first reaction vessel 1, second reaction vessel 2, (n−1)th reaction vessel 3 and (n)th reaction vessel 4. In FIG. 3, n represents an integer of not less than 4. In the apparatus shown in FIG. 3, the (m)th (m≥2) reaction vessel is connected to the (m−1)th reaction vessel via a tube communicating with the insides of these reaction vessels at positions below the liquid levels such that the content of the (m−1)th reaction vessel can be supplied to the (m)th reaction vessel without using a means of liquid transfer that is accompanied by vigorous stirring, such as a pump. Each of the reaction vessels 1 to 4 has a stirrer 5 and a jacket for temperature control which is not shown. The stirrer 5 has two paddle blades at two different positions along the axial direction of the stirring axis.

The first and second reaction vessels 1 and 2 have acrylonitrile feed tubes 6 and 7, respectively. Each of the acrylonitrile feed tubes 6 and 7 is not in contact with the two paddle blades and, for example, placed such that the feed opening is positioned between the two paddle blades. The first reaction vessel 1 further has an aqueous medium feed tube 8 and a microbial catalyst feed tube 9. The aqueous medium feed tube 8 and the microbial catalyst feed tube 9 are placed, for example, such that both of their feed openings are positioned above the liquid level when the reaction vessel contains the liquid.

To the reaction vessel 1, the aqueous medium and the microbial catalyst are continuously fed at constant rates, and the temperature in the reaction vessel 1 is controlled to a predetermined value. Further, acrylonitrile is continuously fed at a constant rate such that the concentration of acrylonitrile in the aqueous medium in the reaction vessel 1 is kept at a predetermined value. In the first reaction vessel 1, acrylonitrile is quickly dispersed in the aqueous medium, and acrylamide is produced from acrylonitrile by the microbial catalyst. Further, the stirrer 5 is operated at a rate of about 1 to 5 m/s in terms of the moving speed of the tips of the paddle wings (tip speed) in each of the reaction vessels, although the rate may vary depending on the size of each reaction vessel. The first reaction vessel 1 continuously supplies the aqueous medium containing produced acrylamide (reaction liquid) to the second reaction vessel 2, while containing a constant amount of the medium in the first reaction vessel 1.

To the second reaction vessel 2, the reaction liquid from the first reaction vessel 1 is continuously supplied at a constant rate, and the temperature in the reaction vessel 2 is controlled to a predetermined value. Further, acrylonitrile is continuously fed at a constant rate such that the concentration of acrylonitrile in the reaction liquid in the reaction vessel 2 is kept at a predetermined value. Acrylonitrile is quickly dispersed in the reaction liquid, and unreacted acrylonitrile in the reaction liquid is allowed to react by the microbial catalyst in the reaction liquid, to further produce acrylamide in the second reaction vessel 2. The second reaction vessel 2 continuously supplies the reaction liquid to the subsequent reaction vessel, while containing a constant amount of the reaction liquid in the second reaction vessel 2.

To the (n−1)th reaction vessel 3, the reaction liquid from the (n−2)th reaction vessel is continuously supplied at a constant rate, and the temperature in the reaction vessel 3 is controlled to a predetermined value. Unreacted acrylonitrile in the reaction liquid is allowed to react by the microbial catalyst in the reaction liquid, to further produce acrylamide in the (n−1)th reaction vessel 3. The (n−1)th reaction vessel 3 continuously supplies the reaction liquid to the (n)th reaction vessel 4, while containing a constant amount of the reaction liquid in the (n−1)th reaction vessel 3.

In the (n)th reaction vessel 4, the temperature is controlled to a predetermined value, and unreacted acrylonitrile in the reaction liquid is further allowed to react. The vessel continuously discharges the reaction liquid, while containing a constant amount of the reaction liquid. The discharged reaction liquid hardly contains acrylonitrile, and acrylamide is contained in an amount of about 50%. From the obtained reaction liquid, the microbial catalyst is separated, and acrylamide is separated/purified as required according to a conventional method. The separated microbial catalyst may be reused as the microbial catalyst to be fed to the first reaction vessel 1.

Figure 4:
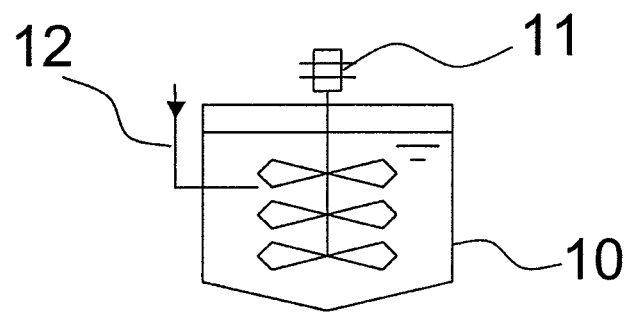
FIG. 4 is a diagram showing another example of the reaction apparatus used in the present invention.

The method by batch reaction can be carried out using, for example, the apparatus shown in FIG. 4. The apparatus shown in FIG. 4 has a reaction vessel 10, a stirrer 11, an acrylonitrile feed tube 12 and a jacket not shown. The reaction vessel 10 contains water, a pH-buffering agent and an aqueous medium containing a microbial catalyst. The stirrer 11 has three paddle blades along the stirring axis. The stirrer 11 is operated such that the tip speed of each paddle blade is about 1 to 5 m/s, although the rate may vary depending on the size of the reaction vessel. The temperature of the aqueous medium is controlled to a predetermined value by the jacket. The acrylonitrile feed tube 12 is not in contact with the paddle blades and, for example, placed such that the feed opening is positioned between the first paddle blade and the second paddle blade.

To the reaction vessel 10, acrylonitrile is continuously or intermittently fed such that acrylonitrile is contained in the aqueous medium in the reaction vessel 10 at a predetermined concentration. The fed acrylonitrile is quickly dispersed in the aqueous medium, and acrylamide is produced from acrylonitrile by the microbial catalyst. By feeding acrylonitrile to an amount predetermined depending on the amount of the aqueous medium in the reaction vessel 10 and keeping stirring the resulting mixture at a predetermined temperature, the acrylonitrile is consumed to produce acrylamide at a concentration of about 50% in terms of the concentration in the reaction liquid in the reaction vessel 10. After completion of the reaction, the microbial catalyst is separated from the reaction liquid, and acrylamide is separated/purified as required.

EXAMPLES

The present invention will now be described in detail by way of Examples and Comparative Examples below. However, the present invention is not restricted by the description below.

(Preparation of Biocatalyst)

The *Rodococcus rhodochrous* J1 strain (deposited with International Patent Organism Depositary, National Institute of Advanced Industrial Science and Technology (AIST; Tsukuba Central 6, 1-1-1 Higashi, Tsukuba, Ibaraki, Japan) under accession No. FERM BP-1478 as of Sep. 18, 1987), which has the nitrile hydratase activity, was aerobically cultured in a medium (pH 7.0) containing 2% glucose, 1% urea, 0.5% peptone, 0.3% yeast extract and 0.05% cobalt chloride (all the contents are expressed in terms of % by mass) at 30° C. The bacterial cells were collected and washed using a centrifuge and 50 mM phosphate buffer (pH 7.0), to obtain a bacterial cell suspension (dry bacterial cells: 12% by mass).

Example 1

In a 1-L stirring vessel equipped with a jacket cooler (inner diameter of the vessel: 10.5 cm), an SUS pipe (inner diameter: 6 mm) was placed as an acrylonitrile feed tube which supplies acrylonitrile, such that the open end (feed opening) of the tube was positioned at a height of 3 cm from the bottom of the vessel. To this stirring vessel, 621 g of 50 mM phosphate buffer (pH 7.0) and 1.5 g of a bacterial cell suspension as a microbial catalyst were fed, and the liquid temperature was controlled to 21° C. by allowing cooling water at 5° C. to flow through the jacket. At this time, the position of the feed opening was 4 cm below the liquid level. The shortest distance between the feed opening and its closest paddle blade was 1 cm.

While the liquid temperature in the vessel was kept at 21° C., acrylonitrile with a purity of 99.7% was fed to the vessel via the acrylonitrile feed tube to start the reaction. During the reaction, the reaction liquid was mixed by stirring with a paddle stirring blade having a blade diameter of 5 cm at a rotation speed of 250 rpm (tip speed, 0.65 m/s). Acrylonitrile was intermittently supplied such that the acrylonitrile concentration in the reaction liquid was constantly 2%. When the accumulated supply of acrylonitrile reached 470 mL, the supply of acrylonitrile was stopped. The reaction was continued until 8 hours had passed since the beginning of the reaction.

Eight hours after the beginning of the reaction, the reaction liquid was subjected to quantitative measurement by the external standard method (absolute calibration method) by gas chromatography (column, PoraPak-PS, manufactured by Waters, 1 m, 180° C.; carrier gas, helium; detector, FID). As a result, 60 ppm unreacted acrylonitrile was detected, and 50.2% acrylamide was detected. The yield of acrylamide from acrylonitrile was 99.3%. The conditions for supplying acrylonitrile and the reaction results are shown in Table 1.

Example 2

The reaction was carried out in the same manner as in Example 1 except that an additional SUS pipe having an inner diameter of 2 mm and a length of 2 cm was connected to the acrylonitrile feed tube such that the open end (feed opening) of this additional pipe was positioned at a height of 3 cm from the bottom of the vessel. The linear velocity of acrylonitrile at the feed opening was 0.04 m/s.

Eight hours after the beginning of the reaction, the reaction liquid was subjected to measurement by gas chromatography in the same manner as in Example 1, and, as a result, 10 ppm unreacted acrylonitrile was detected, and 50.4% acrylamide was detected. The yield of acrylamide from acrylonitrile was 99.7%. The conditions for supplying acrylonitrile and the reaction results are shown in Table 1.

Comparative Example 1

The reaction was carried out in the same manner as in Example 1 except that the feed opening in Example 1 was positioned at a height of 15.5 cm from the bottom of the vessel (4 cm above the final liquid level).

Eight hours after the beginning of the reaction, the reaction liquid was subjected to measurement by gas chromatography in the same manner as in Example 1, and, as a result, 270 ppm unreacted acrylonitrile was detected, and 49.2% acrylamide was detected. The yield of acrylamide from acrylonitrile was 97.4%. The conditions for supplying acrylonitrile and the reaction results are shown in Table 1.

Since more unreacted acrylonitrile remained in Comparative Example 1 compared to Example 1, it was judged that deterioration of the catalyst had proceeded. It is thought that this was caused by insufficient dissolution of acrylonitrile in the reaction liquid, resulting in local existence of acrylonitrile at high concentration, which then lead to promotion of deterioration of the catalyst. Further, as is evident from the concentration of unreacted acrylonitrile and the yield of acrylamide, the amount of evaporation of acrylonitrile to the outside of the reaction system was large.

Comparative Example 2

The reaction was carried out in the same manner as in Example 2 except that the feed opening in Example 2 was positioned at a height of 15.5 cm from the bottom of the vessel (4 cm above the final liquid level).

Eight hours after the beginning of the reaction, the reaction liquid was subjected to measurement by gas chromatography in the same manner as in Example 1, and, as a result, 200 ppm unreacted acrylonitrile was detected, and 48.1% acrylamide was detected. The yield of acrylamide from acrylonitrile was 95.2%. The conditions for supplying acrylonitrile and the reaction results are shown in Table 1. The amount of evaporation of acrylonitrile to the outside of the reaction system was even larger than in Comparative Example 1.

Example 3

Six 1-L stirring vessels each equipped with a jacket cooler (inner diameter of the vessel, 10.5 cm; liquid depth, 11.5 cm) were connected in series. The first vessel was connected to the second vessel through a pipe communicating with the insides of these vessels at positions expected to be below the liquid levels during the reaction. Similarly, the second vessel and the third vessel, the third vessel and the fourth vessel, the fourth vessel and the fifth vessel, and the fifth vessel and the sixth vessel are connected to each other. In the sixth vessel, a pipe for discharging the liquid in the vessel was provided at the bottom of the vessel.

In each of the first, second and third vessels, an SUS pipe for feeding acrylonitrile (inner diameter, 6 mm) was provided as an acrylonitrile feed tube such that the open end (feed opening) of the tube was positioned at a height of 3 cm from the bottom of the vessel (8.5 cm below the liquid level).

Further, to the first vessel, an aqueous medium feed tube for feeding 50 mM phosphate buffer (pH 7.0) as the aqueous medium and a microbial catalyst feed tube for feeding a bacterial cell suspension as the microbial catalyst (both of these were made of polyethylene) were attached. The aqueous medium supply tube was placed such that the open end of the tube was positioned at a height of 5 cm from the bottom of the vessel, and the microbial catalyst feed tube was placed such that the open end of the tube was positioned 3 cm above the liquid level of the reaction liquid.

While the contents of the first to sixth vessels were stirred using paddle blades with a blade diameter of 5 cm at a rotation speed of 250 rpm, 50 mM phosphate buffer (pH 7.0), acrylonitrile and the bacterial cell suspension were continuously fed to the first vessel at rates of 511 mL/hr, 174 mL/hr and 1.5 g/hr, respectively; only acrylonitrile was continuously fed to the second vessel at a rate of 136 mL/hr; and only acrylonitrile was continuously fed to the third vessel at a rate of 77 mL/hr.

In the first vessel, the concentration of acrylonitrile in the reaction liquid was 2.0%; the linear velocity of acrylonitrile in the acrylonitrile feed tube was 0.0017 m/s; the linear velocity of acrylonitrile at the feed opening was also 0.0017 m/s; and the concentration of the microbial catalyst was 0.027%.

In the second vessel, the concentration of acrylonitrile in the reaction liquid was 1.8%; the linear velocity of acrylonitrile in the acrylonitrile feed tube was 0.0013 m/s; the linear velocity of acrylonitrile at the feed opening was also 0.0013 m/s; and the concentration of the microbial catalyst was 0.024%.

In the third vessel, the concentration of acrylonitrile in the reaction liquid was 1.9%; the linear velocity of acrylonitrile in the acrylonitrile feed tube was 0.00076 m/s; the linear velocity of acrylonitrile at the feed opening was also 0.00076 m/s; and the concentration of the microbial catalyst was 0.022%.

The purity of the raw material acrylonitrile was 99.7%. The temperatures of the reaction liquids in the first to sixth vessels were controlled to 24° C., 25° C., 25° C., 26° C., 26° C. and 26° C., respectively, using cooling water (5° C.) in the jacket. Further, the volume of the reaction liquid in each of the first to sixth vessels was adjusted to 1 L, and the reaction liquid continuously discharged from the sixth vessel was collected as the final product.

Two days after the beginning of the reaction, the reaction liquid discharged from the sixth vessel was subjected to measurement by gas chromatography (column, PoraPak-PS, manufactured by Waters, 1m, 180° C.; carrier gas, helium; detector, FID) in the same manner as in Example 1.

As a result, 30 ppm unreacted acrylonitrile was detected, and 50.4% acrylamide was detected. The yield of acrylamide from acrylonitrile was 99.7%. The conditions for supplying acrylonitrile and the reaction results are shown in Table 1.

Example 4

The reaction was carried out in the same manner as in Example 3 except that the open end (feed opening) of the acrylonitrile feed tube in each of the first to third vessels was positioned at a height of 10 cm from the bottom of the vessel (1.5 cm below the liquid level).

Two days after the beginning of the reaction, the reaction liquid discharged from the sixth vessel was subjected to measurement in the same manner as in Example 1. As a result, 90 ppm unreacted acrylonitrile was detected, and 50.3% acrylamide was detected. The yield of acrylamide from acrylonitrile was 99.5%. The conditions for supplying acrylonitrile and the reaction results are shown in Table 1.

Example 5

The reaction was carried out in the same manner as in Example 3 except that, similarly to Example 2, an additional SUS pipe having an inner diameter of 2 mm and a length of 2 cm was connected to the acrylonitrile feed tube in each of the first to third vessels such that the open end (feed opening) of this additional pipe was positioned at a height of 3 cm from the bottom of the vessel.

The linear velocity of acrylonitrile at the feed opening was 0.015 m/s in the first vessel. The linear velocity of acrylonitrile at the feed opening was 0.012 m/s in the second vessel.

Further, the linear velocity of acrylonitrile at the feed opening was 0.0068 m/s in the third vessel.

Two days after the beginning of the reaction, the reaction liquid discharged from the sixth vessel was subjected to measurement in the same manner as in Example 1. As a result, unreacted acrylonitrile was not detected, and 50.5% acrylamide was detected. The yield of acrylamide from acrylonitrile was 99.9%. The conditions for supplying acrylonitrile and the reaction results are shown in Table 1.

Comparative Example 3

The reaction was carried out in the same manner as in Example 3 except that the open end (feed opening) of the acrylonitrile feed tube in each of the first to third vessels was positioned 5 cm above the liquid level of the reaction liquid.

Two days after the beginning of the reaction, the reaction liquid discharged from the sixth vessel was subjected to measurement in the same manner as in Example 1. As a result, 280 ppm unreacted acrylonitrile was detected, and 49.1% acrylamide was detected. The yield of acrylamide from acrylonitrile was 97.2%. The conditions for supplying acrylonitrile and the reaction results are shown in Table 1.

Since, similarly to Comparative Example 1, more unreacted acrylonitrile remained compared to Example 3, it was judged that deterioration of the catalyst had proceeded. It is thought that this was caused by insufficient dissolution of acrylonitrile in the reaction liquid, resulting in local existence of acrylonitrile at high concentration, which then lead to promotion of deterioration of the catalyst. Further, the amount of evaporation of acrylonitrile to the outside of the reaction system was large.

Comparative Example 4

The reaction was carried out in the same manner as in Example 5 except that the additional pipe in each of the first to third vessels was placed such that the open end (feed opening) of the pipe is positioned 5 cm above the liquid level of the reaction liquid.

Two days after the beginning of the reaction, the reaction liquid discharged from the sixth vessel was subjected to measurement in the same manner as in Example 1. As a result, 190 ppm unreacted acrylonitrile was detected, and 48.4% acrylamide was detected. The yield of acrylamide from acrylonitrile was 95.8%. The conditions for supplying acrylonitrile and the reaction results are shown in Table 1. The amount of evaporation of acrylonitrile to the outside of the reaction system was large.

TABLE 1

| | Reaction | Position of feeding of acrylonitrile | Inner diameter of acrylonitrile feed opening [mm] | Unreacted acrylonitrile [ppm] | Produced acrylamide [%] | Reaction yield [%] |
|---|---|---|---|---|---|---|
| Example 1 | Batch | 4 cm below liquid level | 6 | 60 | 50.2 | 99.3 |
| Example 2 | | 4 cm below liquid level | 2 | 10 | 50.4 | 99.7 |
| Comparative Example 1 | | 4 cm above liquid level | 6 | 270 | 49.2 | 97.4 |
| Comparative Example 2 | | 4 cm above liquid level | 2 | 200 | 48.1 | 95.2 |
| Example 3 | Continuous | 8.5 cm below liquid level | 6 | 30 | 50.4 | 99.7 |
| Example 4 | | 1.5 cm below liquid level | 6 | 90 | 50.3 | 99.5 |
| Example 5 | | 8.5 cm below liquid level | 2 | 0 | 50.5 | 99.9 |
| Comparative Example 3 | | 5 cm above liquid level | 6 | 280 | 49.1 | 97.2 |
| Comparative Example 4 | | 5 cm above liquid level | 2 | 190 | 48.4 | 95.8 |

Industrial Applicability

By the production method of the present invention, the reaction yield of acrylamide from acrylonitrile upon production of acrylamide using a biocatalyst can be easily enhanced. Further, since evaporation of acrylonitrile to the outside of the reaction system can be prevented, the method can be suitably used as a method for producing acrylamide at low cost, with less energy and with less environmental load.

Description of Symbols
  1-4, 10 Reaction vessel
  5, 11 Stirrer
  6, 7, 12 Acrylonitrile feed tube
  8 Aqueous medium feed tube
  9 Microbial catalyst feed tube

What is claimed is:

1. A method for producing acrylamide in an aqueous medium by feeding acrylonitrile to said aqueous medium supplemented with a microbial catalyst(s) while stirring said aqueous medium, comprising:
    placing, in said aqueous medium, a feed opening of an acrylonitrile feed tube that feeds acrylonitrile to said aqueous medium to prevent an evaporation of acrylonitrile into gas phase and to enhance a reaction yield of acrylamide from acrylonitrile, wherein the feed opening is positioned at not more than 50 cm distant from a tip of a stirring blade; and feeding acrylonitrile into said aqueous medium,
    wherein linear velocity of acrylonitrile at the feed opening is not less than 0.05 m/s and
    wherein said feed opening has an opening area smaller than the cross-sectional area of said acrylonitrile feed tube.

* * * * *